United States Patent [19]

Hirota et al.

[11] Patent Number: 4,717,501

[45] Date of Patent: Jan. 5, 1988

[54] PEARL LUSTER DISPERSION

[75] Inventors: Hajime Hirota, Tokyo; Shinichi Isoda, Choufu; Hiroshi Watanabe, Funabashi, all of Japan

[73] Assignee: Kao Corporation, Tokyo, Japan

[21] Appl. No.: 786,755

[22] Filed: Oct. 11, 1985

Related U.S. Application Data

[62] Division of Ser. No. 482,441, Apr. 6, 1983.

[30] Foreign Application Priority Data

May 28, 1982 [JP] Japan ................................. 57-90921

[51] Int. Cl.$^4$ ............................................. B01J 13/00
[52] U.S. Cl. ..................................... 252/311; 252/550; 252/551; 252/548; 252/DIG. 13; 252/312; 424/70
[58] Field of Search ........ 252/550, 551, 548, DIG. 13, 252/311, 312; 424/270

[56] References Cited

U.S. PATENT DOCUMENTS 4,148,762 4/1979 Koch ..................... 252/DIG. 13

FOREIGN PATENT DOCUMENTS 0034846 9/1981 European Pat. Off. .
133400 10/1981 Japan .

OTHER PUBLICATIONS

Derwent Abstract, Accession No. 81-55942 D/31, Japanese Patent #J56071021-A, Jun. 13, 1981.
Patent Abstracts of Japan, vol. 5, No. 136 (C-69) (808) Aug. 28, 1981.

Primary Examiner—Josephine L. Barr
Attorney, Agent, or Firm—Oblon, Fisher, Spivak, McClelland & Maier

[57] ABSTRACT

A thick pearl luster dispersion comprising the following four components (A), (B), (C) and (D);
(A) 15–40 wt % of a fatty acid glycol ester,
(B) 0.3–12.5 wt % of an alkylsulfate or polyoxyalkylene alkylsulfate,
(C) 3–25 wt % of a fatty acid dialkanolamide,
(D) 45–85 wt % of water,
the mixing ratios of the (B), (C) and (D) components lying within the area surrounded by straight lines obtained by connecting the determined four points on the triangular cordinate of the three-component system.

A thick pearl luster dispersion according to the invention is uniform in crystalline form, low in viscosity and beautiful in appearance with excellent high and low temperature stability.

1 Claim, 1 Drawing Figure

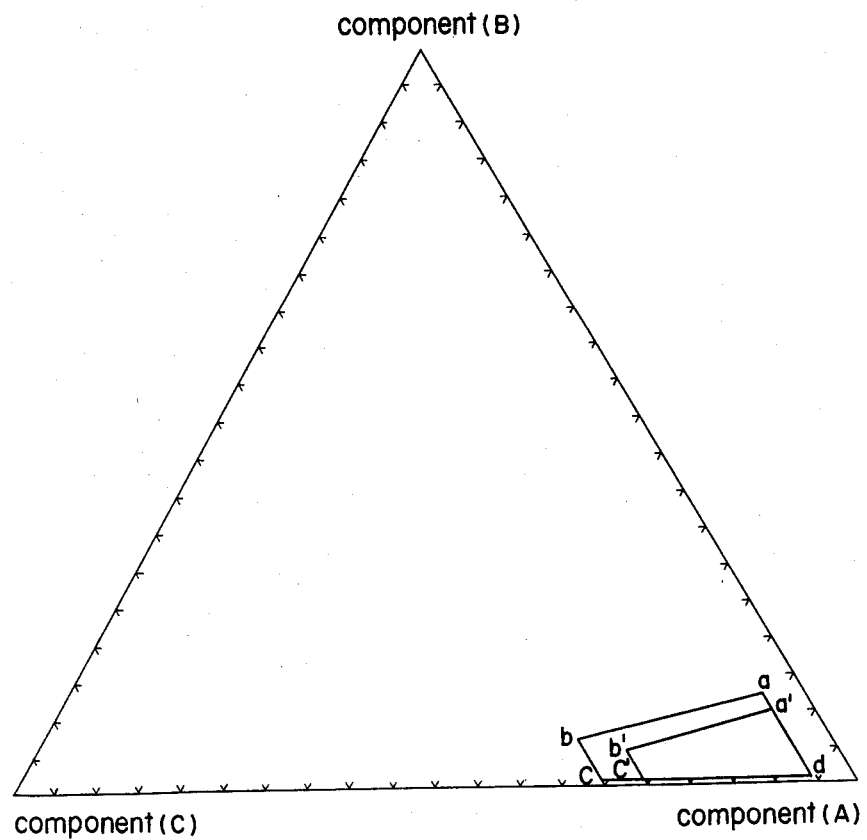

PEARL LUSTER DISPERSION

This is a division of application Ser. No. 482,441, filed Apr. 6, 1983.

BACKGROUND OF THE INVENTION (i) Field of the Invention:

This invention relates to a thick pearl luster dispersion and more particularly, to a thick pearl luster dispersion which is obtained by mixing large amounts of fatty acid glycol esters with a specific type of solvent, and heating and cooling the mixture to precipitate the resulting product as crystals whereby the dispersion becomes uniform in shape of crystals and low in viscosity with excellent high and low temperature stability.

(ii) Description of the Prior Art:

In order to enhance the commercial value of shampooes, rinses, hair-washing creams, liquid detergents and the like, it is the usual practice that these compositions are controlled to have pearl luster appearance. This practice has been realized, for example, by several techniques including mixing of powdered natural products such as mica, fish scales, bismuth oxychloride and the like and inorganic materials, and crystallization of polyvalent metal salts of higher fatty acids, and fatty acid glycol esters in these compositions.

Among these techniques, the currently, widely employed technique is a method using fatty acid glycol esters. In this method, materials which are solid at a normal temperature are added upon preparation of shampoo or the like and after heating and melting, are again cooled for recrystallization to impart pearl-like gloss thereto. Also, there are known methods such as disclosed in Japanese Patent Publication No. 47-804 and Japanese Laid-open Specification No. 5671021 in which fatty acid glycol esters are first molten and cooled to give a pearl luster dispersion and mixed with starting materials for shampoo or the like at a normal temperature.

The method of Japanese Patent Publication No. 47-804 makes use of fatty acid glycol esters and fatty acid monoalkylolamides in combination to give pearl luster. In this method, when a pearl luster of high concentration is prepared, its viscosity becomes abnormally high, involving disadvantages in handling on addition of the luster at a normal temperature for the preparation of shampoo or the like. Also, it takes a long time before uniform mixing with other ingredients.

The Japanese Laid-open Specification No. 56-71021 describes a method for preparing a pearl-like luster which comprises a fatty acid esters in high concentrations. However, this method involves the disadvantage that fatty acid glycol esters are scattered with respect to particle size of crystals with nonuniform shape of crystals, making it difficult to give a beautiful pearl luster appearance.

SUMMARY OF THE INVENTION

The present inventors made intensive studies so as to prepare thick pearl luster dispersion which can overcome the disadvantages of the known dispersions. As a result, we found that when fatty acid glycol esters are used in combination with solvents including alkylsulfates or polyoxyalkylene alkylsulfates, fatty acid dialkylolamides and water within specific ranges of amount, there can be obtained thick pearl luster dispersions which are uniform in crystalline form, low in viscosity and beautiful in appearance with excellent high and low temperature stability.

According to the present invention, there is provided a pearl luster dispersion comprising the following four components (A), (B), (C) and (D):

(A) 15–40 wt% of a fatty acid glycol ester represented by the following general formula (I)

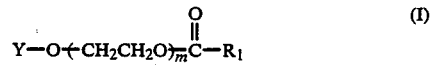

(in which $R_1$ represents a linear or branched, saturated or unsaturated hydrocarbon group having from 13 to 21 carbon atoms, Y represents a hydrogen atom or a group of

and m is an integer of from 1 to 3 and means an average number of addition moles);

(B) 0.3–12.5 wt% of an alkylsulfate or polyoxyalkylene alkylsulfate represented by the following general formula (II)

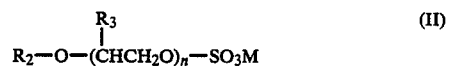

(in which $R_2$ represents a linear or branched alkyl group having from 8 to 20 carbon atoms, $R_3$ represents a hydrogen atom or methyl group, M represents an alkali metal, alkaline earth metal, ammonium ion, ammonium substituted with an alkyl having 1 to 3 carbon atoms, or ammonium substituted with a hydroxyalkyl having 2 or 3 carbon atoms, and n is an integer of 0–8 and means an average number of addition moles);

(C) 3–25 wt% of a fatty acid dialkanolamide represeented by the following general formula (III)

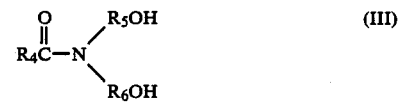

(in which $R_4$ represents a linear or branched, saturated or unsaturated hydrocarbon group having from 7 to 17 carbon atoms, and $R_5$ and $R_6$ independently represent $-C_2H_4$ or $-C_3H_6$); and (D) 45–85 wt% of water, the mixing ratios of the (B), (C) and (D) components lying within an area surrounded by straight lines obtained by connecting the following four points on the triangular cordinate of the three-component system:

a [(B)=12.5:(C)=5: (D)=82.5],
b [(B)=6.25: (C)=30: (D)=63.75],
c [(B)=0.5: (C)=30: (D)=69.5],
d [(B)=0.5: (C)=5: (D)=94.5].

BRIEF DESCRIPTION OF THE DRAWINGS

A sole FIGURE is a triangular cordinate showing mixing ratios of three solvent components used in the present invention.

DETAILED DESCRIPTION OF THE INVENTION AND PREFERRED EMBODIMENTS

Of the fatty acid glycol esters of the formula (I) which are (A) component of the present invention, those esters of the formula in which $R_1$ has 15-17 carbon atoms are preferable because of the best pearl luster. Also, good luster can be obtained in the range of carbon atoms of even 19-21 in case where the number of moles of addition ethylene oxide in the fatty acid glycol ester is 3 or m is 3 in the formula (I). In the formula (I), Y is preferably a group of

This (A) component is one or more of compounds of the formula (I) and is used in an amount of 15-40wt% (hereinafter referred to simply as %), preferably 20-30%, of the pearl luster dispersion.

Preferable alkylsulfates or polyoxyalkylene alkylsulfates of the formula (II) which are the (B) component of the present invention are those of the formula in which $R_2$ is a linear or branched saturated hydrocarbon group having 10-14 carbon atoms on average.

The Starting alcohols for the (B) component may by either natural or synthetic alcohols. The alkylsulfates having oxyalkylene group are preferably those having oxyalkylene group derived from ethylene oxide. The counter ions for the alkylsulfates include alkali metal ions such as sodium, potassium and the like, alkaline earth metal ions such as calcium, magnesium and the like, ammonium ion, and substituted ammonium having 1-3 hydroxyalkyl groups which has 2 or 3 carbon atoms (such as, for example, monoethanolamine, diethanolamine, triethanolamine, triisopropanolamine and the like). Of these counter ions, most preferable ions are sodium ion, ammonium ion and triethanolamine. These (B) components are used in amounts of 0.3-12.5%, preferably 1.0-8%, of the pearl luster dispersion. Less amounts than 0.3% are unfavorable because pearl luster crystals are nonuniform with poor appearance, whereas larger amounts than 12.5% are also unfavorable since the viscosity abnormally increases, leading to a difficulty in handling.

Fatty acid dialkanolamides represented by the formula (III) which are the (C) component of the present invention are preferably those which include starting fatty acids having a distribution of 8-18 carbon atoms and most preferably those containing over 40% of lauric acid ($C_{12}$). Starting alkanolamines are preferably diethanolamine and diisopropanolamine, of which diethanolamine is most preferable. The (C) component is used in amounts of 3-25%, preferably 5-20%, of the dispersion. Less amounts than 3% are not favorable because the (A) component, fatty acid glycol ester, cannot be dispersed satisfactorily, whereas larger amounts than 25% are disadvantageous in that the viscosity excessively increases with pearl luster crystals being nonuniform and thus not beautiful.

Water which is the (D) component of the present invention is not limited with respect to its sources and tap water, deionized water and purified water are all usable.

In the practice of the present invention, the solvents including components (B), (C) and (D) should have ratios defined by an area surrounded by straight lines connecting the following four points on the triangular cordinate of the three-component system shown in FIG. 1:

a [(B)=12.5: (B)=5: (D)=82.5],
b [(B)=6.25: (C)=: (D)=63.75],
c [(B)=0.5: (C)=30: (D)=69.5],
d [(B)=0.5: (C)=5: (D)=94.5].

Preferably, the ratios should lie within an area surrounding by lines connecting the following four points:
a'[(B)=10: (C)=5: (D)=85],
b'[(B)=5: (C)=25: (D)=70],
c'[(B)=0.5: (C)=25: (D)=74.5],
d'[(B)=0.5: (D)=5: (D)=94.5].

In order to prepare the pearl luster dispersion of the present invention, predetermined amounts of (A), (B), (C) and (D) components are charged into a mixing vessel, followed by heating to raise the temperature and agitating. The heating is effected up to a temperature higher than a melting point of (A) component, preferably up to about 80° C. which is higher by over about 50° C. than the melting point. The rate of agitation is not critically limited and rotary agaitation of a speed as low as about 10–100 rpm is adequate. The agitation time under heating conditions is not critical and is in the range of 5–60 minutes, preferably 20–40 minutes, from the viewpoint of operational efficiency. The mixture is heated up to 80° C. and kept as it is while agitating for 30 minutes, whereupon component (A) melts and thus the liquid is emulsified. The resulting emulsion is gradually cooled, while agitating, down to a final liquid temperature of 10°–40° C., preferably 20°–30° C. The manner of cooling is not critically limited and either slow cooling or quenching may be used. When thus cooled, component (A) starts to crystallize at 60° C.–50° C. and an entirety of the liquid assumes beautiful pearl luster thereby obtaining a pearl luster dispersion.

This pearl luster dispersion may comprise, aside from the four components, pH adjusters, preservatives and the like, if necessary. The pH of the dispersion is generally in the range of 4–11, preferably 7–10.

The thus obtained pearl luster dispersion of the present invention can be added to liquid compositions such as liquid shampooes, liquid detergent composition, liquid rinses, and paste compositions in amounts which may vary depending on the purpose, by which beautiful pearl luster can be imparted to these compositions. The amount of the dispersion, for example, in liquid composition is in the range of 1–20%, preferably 2–10%.

The pearl luster dispersion includes therein crystals which are as fine as about 1–10μ and are thus more uniform and have more beautiful appearance than known molten pearl luster dispersions which have particles having sizes over about 30μ.

The dispersion of the present invention is not so high in viscosity and can be admixed with other compositions as a highly concentrated dispersion.

The present invention is particularly described by way of examples which should not be construed as limiting the present invention thereto. Test methods used in examples are as follows.

(1) Appearance

A sample was placed in a transparent glass container with a volume of 100 ml and a degree of pearl luster was visually observed. It will be noted that if bubbles or foams were contained in sample, the sample was subjected to a centrifugal separator for defoaming.

O=Uniform in pearl luster
X=Turbid, emulsified or nonuniform in pearl luster (2) Viscosity A sample used in Test (1) was placed in a thermostat of 30° C. and was kept at a temperature of 30° C., followed by measuring its viscosity by means of the Brookfield viscometer (made by Tokyo Instrument Co., Ltd.)

(3) High Temperature Stability

A sample was placed in a transparent glass container, and after hermetically sealing, was kept in a thermostat of 50° C. for 1 month. Thereafter, the presence or absence of phase separation of the sample and coagulation of the pearl luster was visually observed.

O=No singularities such as separation, coagulation of pearl luster and loss of gloss were recognized.

X=At least one singularity such as separation, coagulation of pearl luster or loss of gloss was recognized.

(4) Low Temperature Stability

A sample was placed in a transparent glass container and after hermetical sealing, was kept in a thermostat of 5° C. for 1 month, followed by visually observing to determine presence or absence of phase separation or solidification of the sample.

O=Fluidity without involving separation and solidification was recognized.

X=Singularities such as separation, solidification and the like were recognized.

EXAMPLE 1

Composition 1

[Ingredients]
Ethylene glycol distearate: 25 parts
Sodium polyoxyethylene (3) laurylsulfate: 3 parts
Coconut oil fatty acid diethanolamide: 6 parts
Water: 66 parts

[Preparation]

The above ingredients were mixed while heating and when the mixture was heated up to 80° C., the ethylene glycol distearate was melted. The mixture was not transparent but was emulsified. This emulsion was cooled down to 30° C. in 2 hours, whereupon a pearl luster dispersion having a uniform particle size and beautiful appearance was obtained.

The dispersion had a viscosity of 2,200 cps (30° C.).

COMPARATIVE EXAMPLE

Composition 2 (Comparison Product)

[Ingredients]
Ethylene glycol distearate: 25 parts
Sodium polyoxyethylene (3) laurylsulfate: 10 parts
Coconut oil fatty acid diethanolamide: 30 parts
Water: 35 parts

[Preparation]

The above ingredients were mixed while heating and when heated up to 80° C., ethylene glycol distearate was melted. The mixture became transparent. When the mixture was cooled down to 30° C., it assumed pearl luster but the particle size was nonuniform with poor appearance.

The resulting dispersion had an apparent viscosity of 123,000 cps (30° C.) with little fluidity.

EXAMPLE 2

Ingredients shown in Table 1 were mixed in different ratios, followed by the procedures of Example 1 and Comparative Example to prepare thick pearl luster dispersions. The resulting dispersions were evaluated with the results shown in Table 1.

TABLE 1

| | | Dispersion Composition No. | | | | | | | | |
|---|---|---|---|---|---|---|---|---|---|---|
| | | 3 | 4 | 5 | 6 | 7 | 8 | 9 | 10 | 11 |
| Ethylene glycol distearate [(A) Component] | | 20% | 20% | 20% | 20% | 25% | 30% | 25% | 35% | 40% |
| Solvents [(B) + (C) + (D)] | | 80% | 80% | 80% | 80% | 75% | 70% | 75% | 65% | 60% |
| Mixing Ratios of Solvents (Parts by wt.) | Ammonium laurylsulfate [(B) Component] | 15 | 5 | 0.4 | 10 | 12.5 | 5 | 1 | 1 | 5 |
| | Lauric acid diethanolamide [(C) Component] | 15 | 35 | 15 | 4 | 5 | 25 | 20 | 5 | 8 |
| | Water [(D) Component] | 70 | 60 | 84.6 | 86 | 82.5 | 70 | 79 | 94 | 87 |
| Viscosity (cps) | | 73,000 | 12,000 | 52,000 | 7,200 | 4,060 | 4,230 | 3,740 | 3,690 | 2,760 |
| Appearance | | x | x | x | x | o | o | o | o | o |
| High temperature stability | | x | x | x | x | o | o | o | o | o |
| Low temperature stability | | x | x | x | o | o | o | o | o | o |

As will become apparent from these results, satisfactory pearl luster dispersions are obtained only when the mixing ratios of the three solvent components (B), (C) and (D) are within a range surrounded by straight lines of the four points a, b, c and d of FIG. 1.

EXAMPLE 3

Pearl luster dispersions of compositions indicated in Table 2 were prepared and evaluated. The preparation and evaluation of the compositions were carried out in the same manner as in Example 2.

TABLE 2

| | | Dispersion Composition No. | | | | | | | | |
|---|---|---|---|---|---|---|---|---|---|---|
| | | 12 | 13 | 14 | 15 | 16 | 17 | 18 | 19 | 20 |
| Component (A) | Triethylene glycol dibehenate | 30% | | 30% | 30% | | 30% | | | 30% |
| | Ethylene glycol monostearate | | 30% | | | 30% | | 30% | 30% | |
| Solvents [(B) + (C) + (D)] | | 70% | 70% | 70% | 70% | 70% | 70% | 70% | 70% | 70% |
| Mixing Ratios of Solvents (parts by wt.) | Component (B) Sodium polyoxyethylene (1) laurylsulfate | 5 | | | | | 5 | | 2.5 | |
| | Triethanolamine laurylsulfate | | 5 | | | | | 5 | | |
| | Sodium laurylsulfate | | | 5 | | | | | 2.5 | 5 |
| | Sodium α-olefin (16 carbon atoms on average) | | | | 5 | | | | | |

TABLE 2-continued

| | | Dispersion Composition No. | | | | | | | | |
|---|---|---|---|---|---|---|---|---|---|---|
| | | 12 | 13 | 14 | 15 | 16 | 17 | 18 | 19 | 20 |
| | sulfate | | | | | | | | | |
| | Sodium laurylbenzensulfonate | | | | | 5 | | | | |
| Component (C) | Lauric acid diethanolamide | 10 | 10 | 10 | 10 | 10 | | | 10 | |
| | Coconut fatty acid monoethanolamine | | | | | | 10 | | | 10 |
| | Lauric acid monoethanolamide | | | | | | | 10 | | |
| Component (D) | Water | 85 | 85 | 85 | 85 | 85 | 85 | 85 | 85 | 85 |
| Appearance | | o | o | o | o | x | o | o | o | o |
| Viscosity (cps) | | 2,200 | 2,160 | 2,640 | 37,820 | 40,200 | 74,300 | 64,700 | 2,680 | 56,400 |
| Low temperature stability | | o | o | o | x | x | x | x | o | x |

What is claimed is:

1. A process for producing a pearl luster dispersion which comprises:

(1) incorporating the following essential components (A), (B), (C) and (D) in the ratio defined by an area surrounded by straight lines obtained by connecting the following four points on the triangular coordinates of the three-component system:

a [(B)=12.5: (C)=5: (D)=82.5],
b [(B)=6.25: (C)=30: (D)=63.75],
c [(B)=0.5: (C)=30: (D)=69.5],
d [(B)=0.5: (C)=5: (D)=94.5], (A) 15 to 40 wt% of a fatty acid glycol ester represented by the following general formula (I)

$$Y-O-(CH_2CH_2O)_{\overline{m}}\overset{O}{\underset{\|}{C}}-R_1 \quad (I)$$

in which $R_1$ represents a linear or branched, saturated or unsaturated hydrocarbon group from 13 to 21 carbon atoms, Y represents a hydrogen atom or a group $$-\overset{O}{\underset{\|}{C}}-R_1$$

and m is an integer of from 1 to 3 and means an average number of addition moles;

(B) 0.3 to 12.5 wt% of an alkylsulfate or polyoxyalkylene alkylsulfate represented by the following general formula (II)

$$R_2-O-(CHCH_2O)_n-SO_3M \quad (II)$$
$$\quad\quad\quad\quad |$$
$$\quad\quad\quad\quad R_3$$

in which $R_2$ represents a linear or branched alkyl group having from 8 to 20 carbon atoms, $R_3$ represents a hydrogen atom or methyl group, M represents an alkali metal, alkaline earth metal, ammonium ion, ammonium substituted with an alkyl having from 1 to 3 carbon atoms, or ammonium substituted with a hydroxyalkyl having 2 or 3 carbon atoms, and n is an integer of 0-8 and means an average number of addition moles;

(C) 3 to 25 wt% of a fatty acid dialkanolamide represented by the following general formula (III)

$$R_4\overset{O}{\underset{\|}{C}}-N\overset{R_5OH}{\underset{R_6OH}{\diagdown}} \quad (III)$$

in which $R_4$ represents a linear or branched, saturated or unsaturated hydrocarbon group having from 7 to 17 carbon atoms, and $R_5$ and $R_6$ independently represent $-C_2H_4$ or $-C_3H_6$; and (D) 45 to 85 wt% of water, (2) heating the thus obtained mixture of components (A), (B), (C) and (D) to a temperature not lower than the melting point of the component (A) to prepare an emulsion, and (3) cooling the emulsion to a temperature lower than the melting point of component (A), thereby obtaining a peal luster dispersion.

* * * * *